US008003823B2

(12) United States Patent
Schneider et al.

(10) Patent No.: US 8,003,823 B2
(45) Date of Patent: *Aug. 23, 2011

(54) HALO ACTIVE AROMATIC SULFONAMIDE ORGANIC COMPOUNDS AND ODOR CONTROL USES THEREFOR

(75) Inventors: David J. Schneider, Union, KY (US); Charles A. Schneider, Villa Hills, KY (US)

(73) Assignees: Charles A. Schneider, Villa Hills, KY (US); David J. Schneider, Union, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/607,188

(22) Filed: Oct. 28, 2009

(65) Prior Publication Data

US 2010/0041761 A1 Feb. 18, 2010

Related U.S. Application Data

(63) Continuation of application No. 11/216,495, filed on Aug. 31, 2005, now Pat. No. 7,629,492, which is a continuation-in-part of application No. 10/369,175, filed on Feb. 18, 2003, now Pat. No. 7,465,829.

(60) Provisional application No. 60/357,265, filed on Feb. 19, 2002.

(51) Int. Cl.
*C07C 303/00* (2006.01)
*C07C 355/00* (2006.01)

(52) U.S. Cl. ............. 564/84; 564/90; 564/99; 558/413; 558/913

(58) Field of Classification Search .................... 564/84, 564/90, 99; 558/413, 913
See application file for complete search history.

(56) References Cited

U.S. PATENT DOCUMENTS

| 2,809,937 | A  | 10/1957 | Gray            |
| 6,296,841 | B1 | 10/2001 | Schneider       |
| 7,465,829 | B2 | 12/2008 | Schneider et al.|

FOREIGN PATENT DOCUMENTS

JP 10-81610 3/1998

OTHER PUBLICATIONS

FDA, Dry Milk Ordinance Supplement 1 Appendix B, pp. 87-88 (1995).
Mullen, The Biocides Business: Regulation, Safety and Applications, pp. 251-266 (2002).
Dawson et al., Inter. Assoc. Fish & Wildlife, Approval of Drugs for Public Fish Production, Second Mid-Year Report of Progress, pp. 1-11, (1995).
Chrzaszewska et al., PL 52046 (CA 69:18848 Best Available, Abstract), (1966).
International Search Report, mailed Apr. 18, 2007.

*Primary Examiner* — Janet L. Andres
*Assistant Examiner* — Raymond Covington
(74) *Attorney, Agent, or Firm* — Richard M. Klein; Fay Sharpe LLP

(57) ABSTRACT

Aromatic N-halosulfonamide organic compounds have been known for over one hundred years. The ability of these compounds to release active halogen ions has been utilized in a range of biocidal and fungicidal applications. The most widely used halogen sulfonamide organic compound for these applications is Chloramine-T. This invention deals with the new use of discovered compositions of matter, halo active aromatic sulfonamide organic compounds and use of solutions of these compounds as, odor control agents. The odor control solutions may be buffered to a predetermined pH. The odor control compositions may further incorporate small percentages of low molecular weight alcohols and wetting agents.

13 Claims, No Drawings

HALO ACTIVE AROMATIC SULFONAMIDE ORGANIC COMPOUNDS AND ODOR CONTROL USES THEREFOR

RELATED APPLICATIONS

This application is a continuation of application U.S. patent application Ser. No. 11/216,495 filed Aug. 31, 2005, which is a continuation-in-part of U.S. Pat. No. 7,465,829, filed Feb. 18, 2003, which claims priority to U.S. Provisional Patent Application Ser. No. 60/357,265, filed Feb. 19, 2002, each of which is hereby incorporated herein by reference in its entirety.

BACKGROUND OF THE INVENTION

Halo active aromatic sulfonamide organic compounds have been known for well over one hundred years. These compounds have been put to a wide range of uses, which include fungicides, biocides, odor control agents, drug reaction intermediates, etc. A widely used sulfonamide organic compound is Chloramine-T. This invention relates to uses for a new class of halo active aromatic sulfonamide organic compounds which have enhanced properties and minimal side effects as compared to the compounds of the prior art. In a broad context this invention relates to the use of halo active sulfonamide compounds in odor control.

While the new compounds of this invention show improvement in a number of potential applications such as; biocides, fungicides, odor control agents, drugs for cultured fish, paint additives, soap additives, stain removers and treat cleansers, this application is particularly concerned with odor control.

When the new halo active aromatic sulfonamide compounds of this invention are used as a biocide, fungicide, odor control agent, or as a treat cleanser, solutions of the sulfonamide compound are brought into contact with the surface being treated. This contact is usually affected by spraying, washing, dipping, and/or mixing in such a manner as to contact the effected surface or substrate with an aqueous formulation of the desired sulfonamide compound or a blended mixture of same.

PRIOR ART

U.S. Pat. No. 6,296,841 discloses the use of Chloramine-T as an odor control agent wherein the Chloramine-T is used with a wetting agent. The disclosure relates primarily to domestic odor control.

A related U.S. Pat. No. 6,743,420 B2 discloses the use of Chloramine-T as an odor control agent wherein the Chloramine-T is used with and without a wetting agent. The disclosure of this patent relates to domestic and industrial odor control.

U.S. Pat. No. 6,667,030 BI, further relates to the use of Chloramine T a an odor control agent.

BRIEF DESCRIPTION OF THE INVENTION

This invention relates to odor control. In the prior art odors were often masked using perfume type substances or by encapsulating odorous molecule. This prior art method of odor control does not destroy or modify the odorous molecule, it only masked the odor. In contrast to the prior art, in accordance with this invention, odors are not controlled by masking or encapsulating but instead odors are controlled by altering or destroying the odor causing molecule.

Odor control is affected in accordance with this invention by treating the odorous substrate with new halo active aromatic sulfonamide organic compounds. These compounds are effective on a wide range of odorous substances as they have the ability to react with odorous molecules, for example aliphatic, aromatic or heterocyclic oxygen, aliphatic, aromatic or heterocyclic sulfur and/or aliphatic, aromatic or heterocyclic nitrogen containing compounds and/or mixtures thereof, in such a manner as to convert these odorous compounds to a non odorous format.

DESCRIPTION OF THE PREFERRED EMBODIMENT

Halo active aromatic sulfonamide organic compounds have been known and used for over one hundred years. Chloramine-T is an example of an old sulfonamide organic compound which has been used in many applications. The usefulness of Chloramine-T is predicated on its ability to release an active Cl+ ion when needed on demand, immediately after which, it simultaneously generates an active aromatic sulfo nitrene companion ion. The active Cl+ ion starts the conversion process of the odor molecule, it is immediately assisted by the companion aromatic sulfo nitrene which completes the conversion process. This process makes the halo active aromatic sulfonamides useful in the odor control, biocidal and fungicidal arts.

The latent halogen cation ion, prior to release by halo active aromatic sulfonamide organic compounds, in accordance with this invention, is relativity covalent. This relative covalency assists to prevent the Cl+ ion from prematurely reacting and as such prevents the active molecule from having detrimental bleaching properties, by remaining bonded until encountering the odor molecule.

The new halo active aromatic sulfonamide compounds as used in this invention have excellent odor control properties. In addition many of these compounds have very low toxicity properties which make them attractive for usage, as odor control agents, in human, animal and aquatic environments.

In its broadest sense the subject invention relates to a process for odor control which comprises treating a substrate containing an odorous substance, with a solution which has an active aromatic N-halosulfonamide.

While any halo active aromatic sulfonamide is functional in accordance with this invention, chloro active sulfonamides are preferred.

The new halo active aromatic sulfonamide compounds which contain at least one halo active sulfonamide group, in accordance with this invention, are in accordance with the following Formulas I to IV.

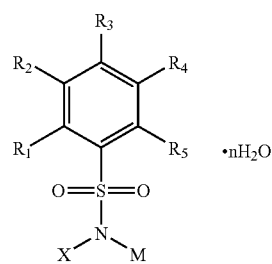

Formula I wherein, X is a halogen,

R3 is hydrogen, methyl, or COOM,

R1, R2, R4, R5 are hydrogen, COOH, derivatized COOH, an ester or alkylated amide, COOM, CN, $NO_2$, $SO_3H$ or derivatized $SO_3R$, a halogen, a substituted or unsubstituted phenyl group, a sulfonamide, a halosulfonamide, a straight or branched aliphatic moiety from $C_1$ to $C_{12}$, wherein, the same straight or branched aliphatic moiety may contain substitution at one or more of the aliphatic hydrogens, and R1, R2, R4 and R5 are other than all hydrogen, and M is an alkali or alkaline earth metal.

Additional compounds which are useful in the subject invention are in accordance with Formula II:

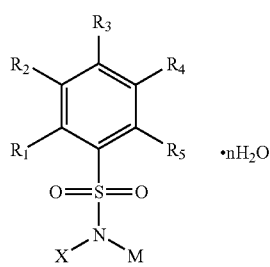

Formula II wherein, X is a halogen,

R1, R2, R4, R5 are hydrogen, COOH, derivatized COOH, an ester or alkylated amide, COOM, CN, $NO_2$, $SO_3H$ or derivatized $SO_3R$, a halogen, a substituted or unsubstituted phenyl group, a sulfonamide, a halosulfonamide, a straight or branched aliphatic moiety from $C_1$ to $C_{12}$, wherein, the same straight or branched aliphatic moiety may contain substitution at one or more of the aliphatic hydrogens.

R3 is an organic derivatized COOH, such as an ester or alkylated amide, CN, $NO_2$, $SO_3H$ or derivatized $SO_3R$, a halogen, a substituted or unsubstituted phenyl group, a sulfonamide, a halosulfonamide, a straight or branched aliphatic moiety from $C_2$ to $C_{12}$, wherein, the same straight or branched aliphatic moiety may contain substitution at one or more of the aliphatic hydrogens, and M is an alkali or alkaline earth metal.

Other compounds which are useful in this invention as odor control agents are as per Formula III:

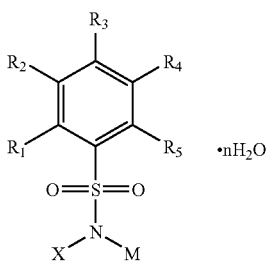

Formula III wherein, X is a halogen,

R1, R2, R4, R5 are hydrogen,

R3 is hydrogen, methyl, or COOM, and M is either potassium, rubidium, cesium, lithium or an alkaline earth metal.

Other compounds which can be used as odor control agents are in accordance with Formula IV:

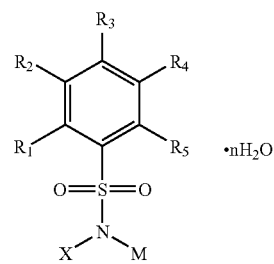

Formula IV wherein, X is bromine, fluorine, or iodine,

R1, R2, R4, R5 are hydrogen,

R3 is hydrogen, methyl, or COOM, and M is an alkali or alkaline earth metal.

Compounds of Formulas I-IV may or may not be hydrated (n $H_2O$), but are generally isolated as a trihydrate where (n=3).

The compounds of Formulas I-IV are very soluble in water. This property allows for easy compounding of odor control compositions and allows high percentages of the compounds to be formulated into the useful solution products.

Further the compounds of Formulas I-IV have minimal bleach odor. This property again is highly advantageous, because, formulations with strong bleach odor are undesirable in most applications.

The activity of the aromatic chlorosulfonamido group of the compounds of Formulas I-IV is regulated by the selection of specific "R" groups. "R" groups adjacent to the chlorosulfonamido group ($R_1$ and $R_5$) can cause steric effects and therefore change activity and/or cause stability changes on the chlorosulfonamido group. In addition the various "R" groups can be effected differently. Specific increases or decreases in activity and, stability may be noted. The usefulness of specific aromatic chlorosulfonamido groups may be affected by their different and unique inductive or resonance effects.

Bleach is commonly used as a source of Cl+ cations which are effective as deodorizers. Because of the problems associated with the use of bleach, i.e. the discoloration of the substrate, and its heavy non discrete oxidizing power, it is generally not suitable for use as a deodorizer. In addition the Cl+ cation which is produced by bleach is much more ionic and non discrete in its reactions when compared to the Cl+ cation produced by the compounds of Formulas I-IV. Further, as the compounds of Formulas I-IV liberate the Cl+ ion, a companion ion an aromatic sulfo nitrene, is released which also is intimately involved in a reaction to convert the odorous molecule to a non-odorous state. That is when compared to the Cl+ cation produced by bleach, the Cl+ cation produced by the compounds of Formulas I-IV is much more covalent and less ionic and therefore is very selective in its initial reaction as a deodorizer, hence, it will attack the odor source and not the substrate. As a result of this covalence the bleaching side effects resulting from the Cl+ cation produced by the compounds of Formulas I-IV do not cause the bleaching problems produced by bleach. Therefore, the Cl+ cation produced by the compounds of Formulas I-IV can be used to deodorize as they do not have side effects such as strong bleach smell etc. Generally it could be said that the compounds of Formulas I-IV are more stable than bleach and have a higher selectivity as a Cl+ source as compared to the Cl+ cation produced by bleach. In addition, the N-halogenated aromatic sulfonamide when activated by an attack on an odorous molecule by its Cl+, further produces an active aromatic sulfo nitrene which also modifies the odor causing molecule in such a manner that it is no longer an odorous molecule.

In summary, compared to bleach the compounds of Formulas I-IV are superior deodorizing agents because they are more selective, more covalent Cl+ and because the backbone companion ion, the aromatic sulfo nitrene, remaining after the Cl+ cation is released from the compounds of Formulas I-IV, is itself very selective but very active and immediately contributes its odor controlling power. This backbone companion ion has the ability to further react with the odor containing molecule thereby permanently removing it as a potential source of odor. In contrast the chemical moiety which remains after the Cl+ cation is removed from bleach has no ability to react with odor causing molecules.

Examples of some specific halo active aromatic sulfonamide compounds that are useful as odor control agents in accordance with this invention are as follows:

1. N-chloro-2-tolylsulfonamide sodium salt
having the following Formula:

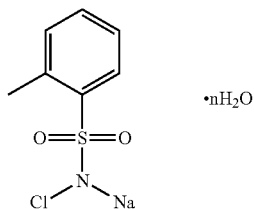

2. N-chloro-4-chlorobenzenesulfonamide sodium salt
having the following Formula:

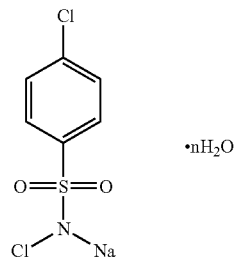

3. N-chloro-2-chlorobenzenesulfonamide sodium salt
having the following Formula:

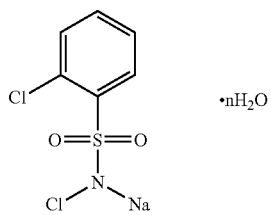

4. N-chloro-4-methoxybenzenesulfonamide sodium salt
having the following Formula:

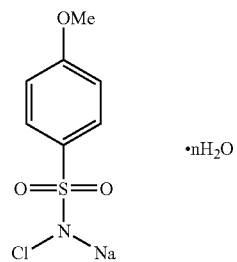

5. N-chloro-2,4,6-mesitylsulfonamide sodium salt
having the following Formula:

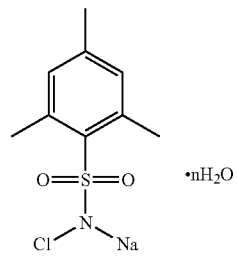

6. N-chloro-4-carboxybenzenesulfonamide dipotassium salt
having the following Formula:

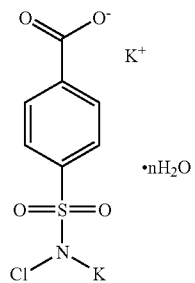

7. N-chloro-4-tolylsulfonamide potassium salt,
having the following Formula:

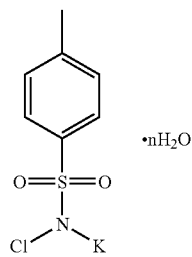

8. N-chloro-4-fluorobenzenesulfonamide sodium salt, having the following Formula:

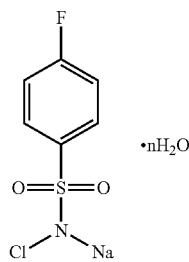

9. N-chloro-4-nitrobenzenesulfonamide sodium salt, having the following Formula:

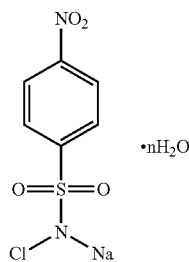

The use of wetting agents with various solutions in order to reduce surface tension is common in the prior art. For example wetting agents are commonly added to herbical solutions to allow the herbicide to wet out plant leaves, likewise the use of wetting agents with insecticides is common.

Most odor causing molecules are mercaptans, sulfides, nitrogen and/or oxygen based compounds. The compounds of Formulas I-IV are excellent agents for eliminating odors which are mercaptan, sulfides, nitrogen and/or oxygen based compounds since both the Cl+ cation and the aromatic sulfo nitrene made available by the compounds of Formula 1 react with and modify the odor causing molecules to create a chemical moiety which has no odor.

In order for the compounds of Formulas I-IV to be effective they must come into contact with the substance which is responsible for the odor. If the substance which is responsible for the odor is in an environment which makes access difficult, i.e. pet stains in a carpet, a means must be provided for bringing the selected compound of Formulas I-IV into contact with the odor causing substance. In many instances when aqueous solution is used as the delivering medium the solution tends to bead up on the substrate. Therefore, when the water component of the solution evaporates the substance in solution is deposited only in localized areas. In the case at hand if an aqueous solution of a compound of Formulas I-IV were applied to a carpet containing a pet stain, the solution would bead up on the carpet, such that when the water evaporates the placement the two reactive components of the molecule would not be such that they could react with the entire odor causing substance on a molecular basis. That is the reaction of the odor control compound with the pet odor and/or stain would be incomplete, and hence the odor control would be incomplete.

In accordance with one embodiment of this invention a substance is added to the solutions of this invention to reduce the surface tension of the solution. As is discussed above the selected compound of Formulas I-IV functions in part by the reaction of the Cl+ moiety with the odor causing molecule. One aspect of this invention is concerned with the fact that many substances which are suitable for reducing the surface tension of the solution may adversely affect the formation of the Cl+ moiety, from the compounds of Formulas I-IV, or degrade said Cl+ moiety once it is formed.

Suitable substances which are useful for reducing the surface tension of the odor control solutions of this invention are synthetic and natural wetting agents. Wetting agents are generally classified as cationic, anionic, amphoteric and nonionic. Because there are thousands of natural and synthetic wetting agents it is impossible to make generalizations as to which wetting agent would be effective in the composition of this invention. With this caveat it can be said that generally the most preferred wetting agents for use in accordance with odor control compositions are anionic wetting agents, with the next preferred class of wetting agents being a nonionic wetting agents.

Amphoteric and cationic wetting agents are least preferred for use with the wetting agent embodiment of this invention.

Regardless of the above comments satisfactory agents may be found in any class of wetting agents.

While the applicant is aware of the vast range of wetting agents available, the applicant is not sure of all ramifications of how different wetting agents degrade the Cl+ moiety. It is felt that functional groups such as alkenes, alcohol, ketone, especially aliphatic ketones or aldehydes containing at least one alpha hydrogen next to the carbonyl carbon, and phenols as may be contained on the base wetting agent molecule are particularly harmful to the Cl+ moiety. Further while it is impossible for the applicant to explore all the ramifications thereof, impurities as may be contained in various commercially available wetting agents can play a significant part in the degradation of the Cl+ moiety. Impurities which are known to facilitate the degradation of the Cl+ moiety are aromatic and conjugated phenols, compounds containing activated carbonyl, alpha aliphatic hydrogen's or active primary and secondary amines.

The concentration of the wetting agent used in accordance with the odor control solutions of this invention can be from about 0.1 to 5%. A more preferred concentration for the wetting agent is from about 0.5 to about 1.5%. In order to achieve maximum efficiency in the odor control proceed the surface tension of the solution must be reduced, so that the compounds of Formula I can reach and react with the odor causing molecules.

A factor in choosing the concentration of the wetting agent is the degree to which it foams. If undesirable foaming occurs anti foamers may be added to the solution.

For stability and for optimum performance as an odor killing agent the pH of a solution of the compounds of Formulas I-IV should be between 6-14, with a more preferred pH range being between 8-9.5 with a most preferred range being between 8.5-9.

As is discussed above the pH range for odor control solutions for use in the invention can be from about 6-14. Below a pH of 6 the compounds of Formulas I-IV tend to decompose due to the acidic nature of the medium. While the solutions of this invention are effective above a pH of 10.0 solutions having a pH of above 10.0 can only be used for industrial applications, due to their caustic nature.

Aromatic N-Halo active sulfonamide solutions for use in this invention exhibit excellent stability at a pH range of 8-9.5. This stability is important in the domestic applications of this invention where long shelf life is very desirable.

Buffering agents which are suitable for use in accordance with this invention are sodium bicarbonate, potassium bicarbonate, sodium carbonate, potassium carbonate, acetate buffers (such as sodium acetate), phosphate buffers (such as tri and di sodium phosphate and mixtures thereof, pH blended phosphates, sulfate buffers (such as di and tri sodium sulfate and mixtures thereof.

Because of price, ease of use, low toxicity and their effect on the environment, the above listed sodium and potassium bicarbonates are preferred buffering agents for use in this invention. Buffered solutions are advantageous in that the active ingredients of the odor control solution of this invention can be shipped in powdered form and mixed by the consumer with no adverse effect.

The concentration of the buffering agent can be from 0.1% up to the limit of solubility. The preferred range for the concentration of the buffering agent is from about 5% to about 200% of the active compound in solution. A more preferred range is from about 5% to about 50% with a most preferred concentration being 25-50%.

The buffering of the solution compensates for any change in pH that may result from the conditions of application, the type of substrate, or industrial waste and the nature of the odor causing molecule.

For the industrial odor control it is preferred that the concentration of a compound of Formula I be about 5-100%. For residential consumer use the concentration of the active ingredient can be from about 0.25 to about 2.0%, with a more preferred range being from about 0.5 to about 1.0% percent, with the most preferred concentration being 0.75%. These lower concentrations keep the bleach like smell to a minimum but still give the desired odor control.

As with all household formulations, it is at times desirable to have a very faint but highly attractive scent associated with its application. Therefore, the use of trace amounts of compatible perfume additives may be used in the formulations of the invention.

Industrial applications for the use of the composition and process of this invention relate to controlling odors which are emitted from a wide variety of industrial sludges such as sewerage treatment sludges, paper making sludges, waste from animal grow outs, animal processing, animal habitats etc.

Paper mills for example are notorious for creating foul odors. In particular the Kraft paper making process produces an odor which is often categorized as a rotten egg smell. In the past, society was tolerant of these odors as society often took the position that the smell of a paper mill was the smell of money. The odor of a paper mill is primarily based on odorous mercaptans, which the human nose can detect at concentrations which approach one part per billion. These paper mill odors originate from the basic chemistry of the paper making process and can be associated with stack gases, holding ponds which are used to hold the sludge which is a byproduct of the paper making process, and from the sludge which results from the treatment of the paper mill stack gases or from solid press.

Odors originating with paper mills can often be detected by humans at distances which can exceed twenty miles. While in the past society was tolerant of these odors in recent times society has become much less tolerant, therefore it is important that these odors be eliminated.

The process and composition of this invention are particularly suited to eliminating paper mill odors due to the ability of the compounds of Formulas I-IV to react with odorous mercaptans.

In accordance with the broadest aspects of this invention paper mill odors can be effectively controlled using solutions of compounds of Formulas I-IV.

The preferred solvent is water, however, other solvents can be used. The solutions which are used to treat Kraft paper mill stack gases or sludge can have a concentration of the compounds of Formula I-IV from about 3 to about 100 percent with a more preferred range being from about 5 to about 12 percent with a most preferred concentration being 8 percent. All concentrations are by weight percent.

In treating paper mill sludge is preferred that the solution be buffered to a pH of about 9.

While a wide variety of buffering agents can be used, the preferred buffering agents for use in treating paper mill sludge are potassium or sodium bicarbonate.

Further, in accordance with the above discussion, the treating solutions for paper mill sludge may incorporate a wetting agent, it is preferred that the solution incorporate a nonionic wetting agent at a concentration of from about 0.1 to about 5 weight percent. The caveats and qualifications for wetting agents as are discussed above likewise apply for the treatment of paper mill sludge's. The preferred wetting agent for use in conjunction with paper mill sludge treating compositions is an anionic wetting agent sold under the trademark Avanel S-74 by the BASF Chemical Co. of Mt. Olive, N.J. The applicant believes that Avanel S-74 is sulfate capped alkyl ethoxylate, where the wetting agent contains 3 units of ethoxylate and the alkyl is a C8 alkyl.

As is discussed above of the compounds of the general Formulas I-IV function as deodorizing agents. The data below demonstrates that the defined aromatic N-halo sulfonamides will control odor, regardless of the specific substation on the structure of Formulas I-IV. This data demonstrates that it is the aromatic N-halo sulfonamide doing the odor control work and the various "R" group combinations will give greater or lesser control of the odor for a given odor problem, however, all of the compounds of Formula I-IV are functional odor control agents. The N-halo sulfonamide is the only common chemical grouping in each of the Formulas. It is safe to say that all aromatic N-halo sulfonamides will show some activity on all odors and conversely a specific N-halo sulfonamide may or may not have the same activity with all odorous compounds.

It has been found that if the deodorizing compositions of this invention further incorporate small percentages of a low molecular weight alcohol, the activity of the deodorizing compound is enhanced.

An example of a suitable alcohol which is useful in conjunction with this aspect of the invention is t-butanol. The effect of the alcohol can manifest itself in many ways. The alcohol enhances the odor removal activity of the active aromatic N-halo sulfonamide group. The alcohol also can make the formulation less difficult, the alcohol can add surface activity, the alcohol can aid in disinfection, the alcohol can enable the use of a more favorable blend of fragrances, surface active compounds and the like, lastly, the alcohol can help stabilize the formulation, etc. The type of alcohol used however is somewhat limited. T-Butanol or related tertiary alcohols are preferred because they do not contain hydrogen atoms alpha to the oxygen alcohol moiety, and therefore offer a more stable formulations. The alpha hydrogens can detract from the stability of the formulations due to interaction with the active halogen contained in the active aromatic halo sulfonamide. However, at pH>10 alcohols containing alpha hydrogens, such as ethanol and isopropanol, were found to be stable in these odor control formulations. In fact, the halo active sulfonamides are stable at high concentrations of alcohols (>50%) at pH>10.

The alcohol can be present at concentrations of from about 0.1 to about 80 weight percent, a more preferred range is from about 0.1 to about 2.0 weight percent with a most preferred range being from about 0.2 to about 1.0 weight percent.

While the applicant does not understand all of the ramifications of why certain alcohols enhance the deodorizing ability of the compounds of Formulas I-IV, it would appear as though the most functional alcohols are those with no hydrogens alpha to the oxygen moiety of the alcohol i.e. CH or $CH_2$ groups next to OH group.

Deodorizing compounds in accordance with this invention can further incorporate small percentages of compatible fragrances, i.e. pine, orange, lemon fragrances.

EXAMPLES

The present invention is illustrated by the following Examples which, however, are not to be construed as limiting the invention to their details.

The following Examples illustrate the general utility of N-Halogenated aromatic sulfonamides in odor control. It has been found that the "R" group substitution has an affect on how effective a given compound is in odor control.

For purposes of conducting the test in accordance with the below listed Examples a series of odorous test reagents were prepared. The utilized odorous test reagents are in accordance with the following:

Onion:

2 g samples of chopped white onion (Approximately ⅛" cubes) were prepared and used for each test.

Garlic:

DMSO (dimethyl sulfoxide) 1 g was used for each test.

Fox Urine:

0.5 g of deer hunter's grade red fox urine was used for each test.

Rotten Egg:

0.1 g of a 5% sodium sulfide solution was added to a beaker and 2 drops of glacial acetic acid was added to prepare the rotten egg scent and used for each test.

Odor Control Solutions:

Unless otherwise specified separate 1% w/w solutions in water of each halo active aromatic sulfonamide derivative were prepared for use. Each solution also contained 0.3% Avenal S-74. The pH of the resulting formulations varied between 8.0 and 9.0.

The testing protocol for Examples 1 thru 12 involved is as follows: The defined odorous reagents were added to a beaker, watch glass, or petri dish. For each aromatic sulfonamide derivative, 3 grams of the formulated odor control solution defined above were sprayed with a trigger sprayer, separately onto each odor (onion, garlic, fox urine, rotten egg. Odor evaluations were then made by a six person human panel.

The evaluation criteria utilized is as follows;

E=Excellent, immediate removal of odor, no remaining odor.

G=Good, Immediate (within seconds) reduction of odor, very slight but detectable trace odor remains.

F=Fair, Immediate (within seconds) reduction, more pronounced odor remains.

P=Detectable reduction in odor but rate of reduction is slow and a much more pronounced odor remains.

All test evaluations were made at 20° C.

Example 1

The structure of halo aromatic sulfonamide compound tested is as follows:

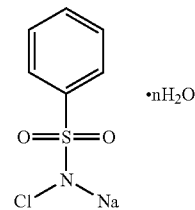

Test odors were prepared and odor evaluation conducted, the resulting test results are as follows:

| Onion | Garlic | Fox Urine | Rotten Egg |
|-------|--------|-----------|------------|
| G     | P      | G         | E          |

Example 2

The structure of halo active aromatic sulfonamide compound tested is as follows:

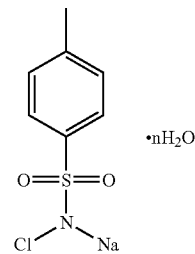

Test odors were prepared and odor evaluation conducted, the resulting test results are as follows:

| Onion | Garlic | Fox Urine | Rotten Egg |
|-------|--------|-----------|------------|
| E     | G      | E         | E          |

Example 3

The structure of halo active aromatic sulfonamide compound tested is as follows:

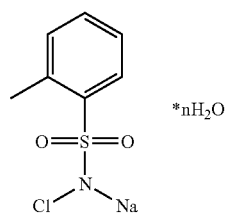

Test odors were prepared and odor evaluation conducted, the resulting test results are as follows:

| Onion | Garlic | Fox Urine | Rotten Egg |
|-------|--------|-----------|------------|
| E | F | G | E |

Example 4

The structure of halo active aromatic sulfonamide compound tested is as follows:

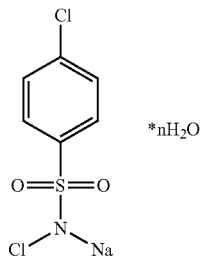

Test odors were prepared and odor evaluation conducted, the resulting test results are as follows:

| Onion | Garlic | Fox Urine | Rotten Egg |
|-------|--------|-----------|------------|
| E | P | G | E |

Example 5

The structure of halo active aromatic sulfonamide compound tested is as follows:

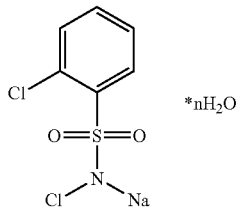

Test odors were prepared and odor evaluation conducted, the resulting test results are as follows:

| Onion | Garlic | Fox Urine | Rotten Egg |
|-------|--------|-----------|------------|
| E | P | E | E |

Example 6

The structure of halo aromatic sulfonamide compound tested is as follows:

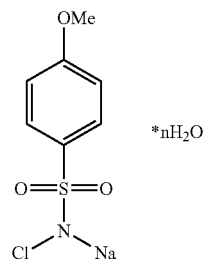

Test odors were prepared and odor evaluation conducted, the resulting test results are as follows:

| Onion | Garlic | Fox Urine | Rotten Egg |
|-------|--------|-----------|------------|
| E | G | E | E |

Example 7

The structure of halo active aromatic sulfonamide compound tested is as follows:

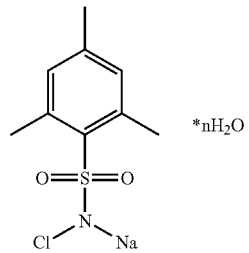

Test odors were prepared and odor evaluation conducted, the resulting test results are as follows:

| Onion | Garlic | Fox Urine | Rotten Egg |
|-------|--------|-----------|------------|
| P | P | P | P |

Example 8

The structure of halo active aromatic sulfonamide compound tested is as follows:

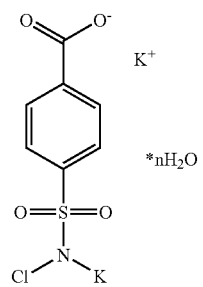

Test odors were prepared and odor evaluation conducted, the resulting test results are as follows:

| Onion | Garlic | Fox Urine | Rotten Egg |
|-------|--------|-----------|------------|
| E     | P      | F         | E          |

Example 9

The structure of halo active aromatic sulfonamide compound tested is as follows:

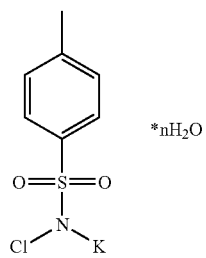

Test odors were prepared and odor evaluation conducted, the resulting test results are as follows:

| Onion | Garlic | Fox Urine | Rotten Egg |
|-------|--------|-----------|------------|
| E     | G      | E         | E          |

Example 10

The structure of halo active aromatic sulfonamide compound tested is as follows:

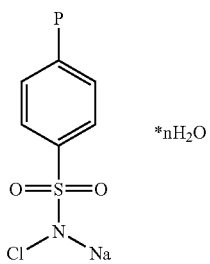

Test odors were prepared and odor evaluation conducted, the resulting test results are as follows:

| Onion | Garlic | Fox Urine | Rotten Egg |
|-------|--------|-----------|------------|
| E     | G      | E         | E          |

Example 11

The structure of halo active aromatic sulfonamide compound tested is as follows:

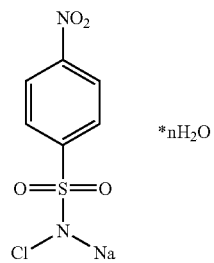

Test odors were prepared and odor evaluation conducted, the resulting test results are as follows:

| Onion | Garlic | Fox Urine | Rotten Egg |
|-------|--------|-----------|------------|
| G     | F      | E         | F          |

Example 12

The structure of halo active aromatic sulfonamide compound tested is as follows:

Test odors were prepared and odor evaluation conducted, the resulting test results are as follows:

| Onion | Garlic | Fox Urine | Rotten Egg |
|-------|--------|-----------|------------|
| E     | F      | E         | E          |

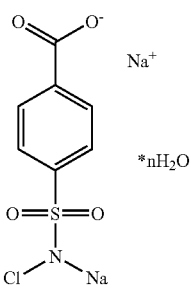

Example 13

Industrial waste water odor. A 100 g sample of an industrial waste water having a strong sulfur type odors were placed in a beaker and treated with 1.0 g of the following formulation.

| Formulation | w/w % |
|-------------|-------|
| N-chloro-4-tolylsulfonamide sodium salt, aka Chloramine-T | 8% |
| Avenal S-74 | 0.3% |
| Sodium Bicarbonate | 2% |
| Water | 89.7% |
| Ph | 8.5 |

An evaluation by a panel of six humans determined that all odor was eliminated.

Example 14

Skunk oil was applied to a 5×5 swatch of nylon pile carpet. The samples had a very noticeable skunk odor. The swatch was treated with 3 pulls of a trigger spray (Approx 2.6 g of the formulation). The odor of the swatch immediately changed from an overbearing skunk odor to no skunk odor using a 6 human panel test.

| The Formulation utilized was: | w/w % |
|---|---|
| 4-tolylsulfonamide sodium salt, aka Chloramine-T | 0.8% |
| Avenal S-74 | 0.03% |
| Sodium Bicarbonate | 0.2% |
| Water | 99% |

Example 15

Garbage disposal odor removal. A used garbage disposal which was found to have residual unpleasant odor after water was continuously run through the disposal for 3 minutes. The garbage disposal was treated with 5 trigger pulls (approximately 4.3 g) of the following solution:

| Formulation | w/w % |
|---|---|
| N-chloro-4-carboxybenzenesulfonamide disodium salt | 1% |
| Avenal S-74 | 0.03% |
| Sodium Bicarbonate | 0.2% |
| Fragrance | 0.1% |
| Water | 98.7% |

A 6 person panel evaluated the odor immediately after application of the solution and found no objectionable odor remained. Water was run through the disposal for approximately 3 minutes and the odor was again evaluated by the panel which found no unpleasant odor.

Example 16

Industrial waste sludge odor. A 100 g sample of industrial waste sludge (solids and aqueous compounds) containing very strong sulfur type odors was placed in a beaker and treated with 2.0 g of the following formulation. The solution was stirred for 1 minute. The formulation utilized is as follows.

| Formulation | w/w % |
|---|---|
| N-chloro-4-carboxybenzenesulfonamide disodium salt | 10% |
| Avenal S-74 | 0.3% |
| Sodium Bicarbonate | 2% |
| Water | 87.7% |

A six person human panel found that all unpleasant odors were eliminated.

Example 17

Dog odor. A used dog bed (approx 30" diameter) containing disagreeable odor was sprayed with 10 trigger pulls (approx. 8.5 g) of the formulation. A 6 person panel determined that all disagreeable odor was immediately eliminated. The formulation utilized is as follows.

| Formulation | w/w % |
|---|---|
| N-chloro-4-carboxybenzenesulfonamide disodium salt | 0.6% |
| N-chloro-4-tolylsulfonamide sodium salt, aka Chloramine-T | 0.3% |
| Avenal S-74 | 0.03% |
| Sodium Bicarbonate | 0.2% |
| t-Butanol | 0.5% |
| Fragrance | 0.1% |
| Water | 98.3% |

Example 18

Cat odor. Used cat litter boxes (approx. 20"×16") all of which had an unpleasant odor were sprayed with 5 trigger pulls (approx. 4.3 g) of the formulation. The litter boxes were evaluated by a panel of 6 humans, after treatment the panel found that the unpleasant odors were eliminated.

The formulation utilized is as follows:

| Formulation | w/w % |
|---|---|
| N-chloro-4-carboxybenzenesulfonamide disodium salt | 0.6% |
| N-chloro-4-tolylsulfonamide sodium salt, aka Chloramine-T | 0.15% |
| Avenal S-74 | 0.03% |
| Sodium Bicarbonate | 0.2% |
| t-Butanol | 0.5% |
| Fragrance | 0.1% |
| Water | 98.4% |

Example 19

To a 5×5 swatch of nylon pile carpet 1 g of fox urine was applied. The swatch was treated with 3 pulls of a trigger spray (approx. 2.6 g of the formulation was sprayed on to the swatch). The odor of the swatch was immediately evaluated by a 6 person panel and found no trace of urine odor.

The formulation utilized is as follows:

| Formulation | w/w % |
|---|---|
| N-chloro-4-carboxybenzenesulfonamide disodium salt | 0.6% |
| N-chloro-4-tolylsulfonamide sodium salt, aka Chloramine-T | 0.3% |
| Avenal S-74 | 0.03% |
| Sodium Bicarbonate | 0.2% |
| t-Butanol | 2% |
| Water | 96.9% |

Example 20

In order to evaluate the stability of various sulfonamide compounds for use in odor control, the stability of N-chloro-4carboxybenzenesulfonamide disodium salt was evaluated at various pHs. A base sulfonamide formulation was prepared in accordance with the following formulation:

| Formulation | w/w % |
| --- | --- |
| N-chloro-4-carboxybenzenesulfonamide disodium salt | 1% |
| Avenal S-74 | 0.03% |
| Sodium Bicarbonate | 0.2% |
| t-Butanol | 1% |
| Water | 97.8% |

The pH of 20 ml sample of the base formulation is 8.7. The temperature of the sample was raised to 50° C. and the sample was allowed to stand for 30 days. At the end of this period it was found that 99.5% of the N-chloro-4-carboxybenzene sulfonamide disodium salt remained.

21. The test protocol of Example 20 was repeated except that the pH of the sample was adjusted to 6.0, with 1N sulfuric acid and the sample was allowed to stand for 1 day. At the end of this period 0%, of the N-chloro-4-carboxybenzenesulfonamide disodium salt remained.

22. The test procedure of Example 20 was repeated, wherein the pH of the sample was adjusted to 6.0 with 1N sulfuric acid and the t-Butanol was replaced with ethanol. The solution was allowed to stand 1 day at which time 0% of the sulfonamide compound remained.

23. The test procedure of Example 20 was repeated where the pH of the sample was 8.7 and the t-butanol was replaced with ethanol. The sample was allowed to stand for 7 days. At the end of this period 0%, the N-chloro-4-carboxybenzenesulfonamide disodium salt remained.

24. The test procedure of Example 20 was repeated, wherein the pH of the sample was adjusted to 10.3 with 1N sodium hydroxide and the t-Butanol was replaced with ethanol. The solution was allowed to stand 30 days at which time 70% of the sulfonamide compound remained.

25. The test procedure of Example 20 was repeated, wherein the pH of the sample was adjusted to 6.0 with 1N sulfuric acid and the t-Butanol was replaced with isopropanol. The solution was allowed to stand 1 day at which time 0% of the sulfonamide compound remained.

26. The test procedure of Example 20 was repeated where the pH of the sample was 8.7 and the t-butanol was replaced with isopropanol. The sample was allowed to stand for 7 days. At the end of this period 50%, the N-chloro-4-carboxybenzenesulfonamide disodium salt remained.

27. The test procedure of Example 20 was repeated, wherein the pH of the sample was adjusted to 10.3 with 1N sodium hydroxide and the t-Butanol was replaced with isopropanol. The solution was allowed to stand 30 days at which time 90% of the sulfonamide compound remained.

Discussion of the Examples

Examples 1 to 27 demonstrate that sulfonamide compounds when used in accordance with this invention exhibit substantial odor control properties. As can be seen from the data of the Examples in all instances the various odors were mitigated to an acceptable level.

Further, the data of Examples 13 to 27 demonstrate the effect of pH on various sulfonamide formulations and the effect of the addition of various low molecular weight alcohols to the formulations.

What is claimed is:

1. A process for controlling odor being emitted by an odor causing material which comprises treating the material with a solution containing an effective amount of a halo active aromatic sulfonamide compound having the formula:

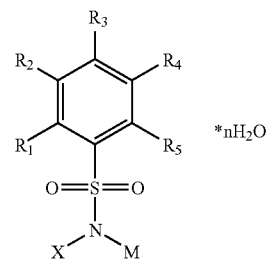

wherein X is a halogen;

$R_3$ is hydrogen, methyl, or COOM;

$R_1$, $R_2$, $R_4$, and $R_5$ are independently selected from hydrogen, COOH, an ester or alkylated amide, COOM, CN, $NO_2$, $SO_3H$, a halogen, a substituted or unsubstituted phenyl group, a sulfonamide, a halosulfonamide, or a straight or branched aliphatic $C_{1-12}$ moiety which may be substituted;

$R_1$, $R_2$, $R_4$ and $R_5$ are other than all hydrogen;

and M is an alkali or alkaline earth metal.

2. The process of claim 1 wherein the solution further incorporates an effective amount of a wetting agent which essentially does not react with the sulfonamide compound.

3. The process of claim 2 wherein the wetting agent is an anionic or nonionic wetting agent.

4. The process of claim 1 wherein the solution is buffered to a pH of from about 7 to about 10.

5. The process of claim 1 wherein the solution is buffered to a pH of from about 8 to about 9.5.

6. The process of claim 1 wherein the solution is buffered with sodium bicarbonate to a pH of from about 8.5 to about 9.

7. The process of claim 1 wherein the pH of the solution is buffered to a pH of greater than 10.

8. The process of claim 1 wherein the concentration of the sulfonamide compound is from about 0.5 to about 10 weight percent.

9. The process of claim 1 wherein the sulfonamide compound has the following Formula:

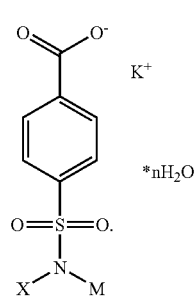

10. The process of claim 1 wherein the solution further incorporates an effective amount of a low molecular weight alcohol.

11. A process for controlling odor being emitted by an odor causing material which comprises treating the material with a solution containing an effective amount of a halo active aromatic sulfonamide compound having the formula:

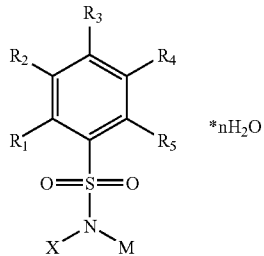

wherein X is a halogen;

$R_1$, $R_2$, $R_4$, and $R_5$ are independently hydrogen, COOH, an ester or alkylated amide, COOM, CN, $NO_2$, $SO_3H$, a halogen, a substituted or unsubstituted phenyl group, a sulfonamide, a halosulfonamide, or a straight or branched $C_{1-12}$ aliphatic moiety which may be substituted;

$R_3$ is halogen; and

M is an alkali or alkaline earth metal.

12. The process of claim 11 wherein the sulfonamide compound has the following Formula:

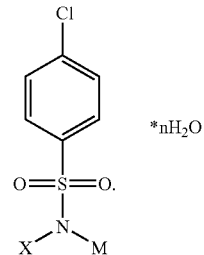

13. The process of claim 11 wherein the sulfonamide compound has the following Formula:

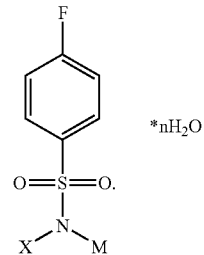

* * * * *